US009486291B2

(12) United States Patent
Bizzell et al.

(10) Patent No.: US 9,486,291 B2
(45) Date of Patent: Nov. 8, 2016

(54) TARGET REGION IDENTIFICATION FOR IMAGING APPLICATIONS

(71) Applicant: Rivanna Medical, LLC, Crozet, VA (US)

(72) Inventors: Daniel Lee Bizzell, Charlotte, NC (US); Raeshon Lamont McNeil, Charlotte, NC (US); Juan Carlos Perez, Charlotte, NC (US)

(73) Assignee: Rivanna Medical LLC, Charlottesville, VA (US)

( * ) Notice: Subject to any disclaimer, the term of this patent is extended or adjusted under 35 U.S.C. 154(b) by 602 days.

(21) Appl. No.: 13/922,324

(22) Filed: Jun. 20, 2013

(65) Prior Publication Data

US 2014/0005542 A1    Jan. 2, 2014

Related U.S. Application Data

(60) Provisional application No. 61/662,481, filed on Jun. 21, 2012.

(51) Int. Cl.
*A61B 8/00* (2006.01)
*A61B 19/00* (2006.01)
*A61B 17/34* (2006.01)

(52) U.S. Cl.
CPC ........... *A61B 19/54* (2013.01); *A61B 17/3403* (2013.01); *A61B 90/13* (2016.02); *A61B 90/39* (2016.02); *A61B 2017/3413* (2013.01); *A61B 2090/395* (2016.02)

(58) Field of Classification Search
None
See application file for complete search history.

(56) References Cited

U.S. PATENT DOCUMENTS

| | | | |
|---|---|---|---|
| 4,476,873 A | 10/1984 | Sorenson et al. | |
| 4,913,157 A | 4/1990 | Pratt, Jr. et al. | |
| 5,623,931 A | 4/1997 | Wung et al. | |
| 5,924,992 A | 7/1999 | Park et al. | |
| 6,126,608 A | 10/2000 | Kemme et al. | |
| 7,141,020 B2 * | 11/2006 | Poland | G01H 1/00 600/437 |
| 7,244,234 B2 | 7/2007 | Ridley et al. | |
| 7,662,128 B2 | 2/2010 | Salcudean et al. | |

(Continued)

FOREIGN PATENT DOCUMENTS

| | | |
|---|---|---|
| WO | WO2006092594 A2 | 9/2006 |
| WO | WO 2011094585 A1 | 8/2011 |

(Continued)

OTHER PUBLICATIONS

P. Foroughi et al., "Ultrasound Bone Segmentation Using Dynamic Programming", IEEE Ultrasonics Symposium, 2007, p. 2523-2526.

(Continued)

*Primary Examiner* — Long V Le
*Assistant Examiner* — Bradley Impink
(74) *Attorney, Agent, or Firm* — Intrinsic Law Corp.; Ibrahim M. Hallaj

(57) ABSTRACT

Systems and methods related to the location of target regions in imaging applications are generally described. Certain embodiments relate to devices and/or methods for image-guided identification of suitable regions at which to insert needles, catheters, and the like. Such systems and methods can be used in association with a variety of imaging technologies, including ultrasound imaging. In certain embodiments, the systems and methods described herein can be used in association with hand-held ultrasound imaging devices.

14 Claims, 14 Drawing Sheets

(56) References Cited

U.S. PATENT DOCUMENTS

| | | | |
|---|---|---|---|
| 7,699,776 | B2 | 4/2010 | Walker et al. |
| 2004/0236217 | A1 | 11/2004 | Cerwin et al. |
| 2005/0085727 | A1* | 4/2005 | Swanborn ............ A61B 5/6842 600/446 |
| 2005/0249391 | A1 | 11/2005 | Kimmel et al. |
| 2007/0106156 | A1 | 5/2007 | Altmann et al. |
| 2007/0167829 | A1 | 7/2007 | Hirsh |
| 2007/0238998 | A1 | 10/2007 | Nycz et al. |
| 2008/0260227 | A1 | 10/2008 | Hayashi et al. |
| 2009/0046912 | A1 | 2/2009 | Hostettler et al. |
| 2010/0016726 | A1 | 1/2010 | Meier |
| 2010/0040268 | A1 | 2/2010 | Boeing et al. |
| 2011/0023585 | A1 | 2/2011 | Izikoff |
| 2011/0054355 | A1* | 3/2011 | Hunter ................ A61B 5/0053 600/587 |
| 2011/0137175 | A1 | 6/2011 | Hossack et al. |
| 2012/0029356 | A1 | 2/2012 | Hossack et al. |
| 2012/0293507 | A1 | 11/2012 | Inoue |
| 2016/0051224 | A1* | 2/2016 | Striano ................ A61B 8/4455 600/461 |

FOREIGN PATENT DOCUMENTS

| | | |
|---|---|---|
| WO | WO 2012148985 A1 | 11/2012 |
| WO | WO2012148985 A1 | 11/2012 |

OTHER PUBLICATIONS

F. W. Mauldin et al., "Three-dimensional spinal bone imaging with medical ultrasound for epidural anesthesia guidance", IEEE International Ultrasonics Symposium Proceedings, 2011, p. 238-241.

K. Owen et al., "Transducer Motion Estimation Using Combined Ultrasound Signal Decorrelation and Optical Sensor Data for Low-cost Ultrasound Systems with Increased Field of View", IEEE International Ultrasonics Symposium Proceedings, 2011, p. 1431-1434.

A. Rasoulian et al., "Augmentation of Paramedian 3D Ultrasound Images of the Spine", IPCAI, 2013, p. 51-60, Springer-Verlag Berlin Heidelberg.

I. Hacihaliloglu et al., "Automatic Bone Localization and Fracture Detection from Volumetric Ultrasound Images Using 3-D Local Phase Features", Ultrasound in Med. & Biol., 2012, p. 128-144, vol. 38, No. 1, World Federation for Ultrasound in Medicine & Biology.

A. Rasoulian et al., "Probabilistic Registration of an Unbiased Statistical Shape Model to Ultrasound Images of the Spine", SPIE, 2012, vol. 8316.

K. Owen et al., "Improved Elevational and Azimuthal Motion Tracker Using Sector Scans", IEEE Transactions of Ultrasonics, Ferroelectrics, and Frequency Control, Apr. 2013, vol. 60, No. 4, IEEE.

D. Shao et al., "Characteristic matching-based adaptive fast bilateral filter for ultrasound speckle reduction", Pattern Recognition Letters, 2013, p. 463-469, vol. 34, Elsevier.

S. Balocco et al., "SRBF: Speckle Reducing Bilateral Filtering", Ultrasound in Med. & Biol., 2010, p. 1353-1363, vol. 36, No. 8, Elsevier.

M. Lang et al., "Noise Reduction Using an Undecimated Discrete Wavelet Transform", IEEE Signal Processing Letters, Jan. 1996, p. 10-12, vol. 3, No. 1, IEEE.

S. Sudha et al., "Speckle Noise Reduction in Ultrasound Images Using Context-based Adaptive Wavelet Threshold", IETE Journal of Research, May/Jun. 2009, p. 135-143, vol. 55, Iss. 3.

F. W. Mauldin Jr., et al., "The Effects of Transducer Geometry on Artifacts Common to Diagnostic Bone Imaging with Conventional Medical Ultrasound", IEEE Transactions on Ultrasonics, Ferroelectrics, and Frequency Control, Jun. 2012, p. 1101-1114, vol. 59, No. 6, IEEE.

J. C. Lazaro et al., "Influence of thresholding procedures in ultrasonic grain noise reduction using wavelets", Ultrasonics, 2002, p. 263-267, No. 40, Elsevier Science B.V.

Chin, Ki Jinn et al. "Ultrasound Imaging Facilitates Spinal Anesthesia in Adults with Difficult Surface Anatomic Landmarks" Anesthesiology, v. 115, No. 1, Jul. 2011.

* cited by examiner

TARGET REGION IDENTIFICATION FOR IMAGING APPLICATIONS

RELATED APPLICATIONS

This application claims priority under 35 U.S.C. §119(e) to U.S. Provisional Patent Application Ser. No. 61/662,481, filed Jun. 21, 2012 and entitled "Target Region Identification for Imaging Applications," which is incorporated herein by reference in its entirety for all purposes.

TECHNICAL FIELD

Systems and methods related to the location of target regions in imaging applications are generally described.

BACKGROUND

Medical ultrasound is commonly used to facilitate needle injection procedures such as central venous line placement or various spinal anesthesia procedures. A commonly implemented technique involves locating anatomical landmarks (e.g. blood vessel or bone structures) using ultrasound and subsequently manually marking the patient's skin with a surgical marker in proximity to the ultrasound transducer. The ultrasound transducer is then removed, and the needle is inserted after positioning the needle at a location relative to the marking sites. The "marking approach" has been demonstrated to increase procedure success rates compared with the "blind approach" (i.e. inserting the needle without using medical imaging) when applied to spinal epidural anesthesia. (See, e.g., K. J. Chin, et al., "Ultrasound Imaging Facilitates Spinal Anesthesia in Adults with Difficult Surface Anatomic Landmarks." *Anesthesiology.* 115(1), 2011, pp. 94-101. doi: 10.1097/ALN.0b013e31821a8ad4. PubMed PMID: WOS:000291925400015).

Current standard ultrasound devices do not offer a mechanism to facilitate accurate skin marking relative to the underlying anatomy while the ultrasound device is in place. Accordingly, improved devices and methods are needed.

SUMMARY

Systems and methods for locating target regions in imaging applications are provided. The subject matter of the present invention involves, in some cases, interrelated products, alternative solutions to a particular problem, and/or a plurality of different uses of one or more systems and/or articles.

Certain aspects relate to devices, including devices used in imaging applications. In one set of embodiments, the device comprises a housing comprising an imaging unit and a working side configured to be placed adjacent a target that is to be imaged. The device further comprises, in certain embodiments, a marking unit configured to produce a mark on the target to be imaged within boundaries of a periphery of the housing.

In some embodiments, the device comprises a housing comprising an imaging unit and a working side configured to be placed adjacent a target that is to be imaged; a plurality of housing alignment indicators configured to indicate reference locations used to locate a target region that is positioned on the target to be imaged and within boundaries of a periphery of the housing; and a template configured to locate the target region based upon the location of the housing alignment indicators.

In one aspect, a kit is provided. The kit comprises, in certain embodiments, a device for performing imaging, comprising a housing comprising an imaging unit and a plurality of alignment indicators configured to indicate reference locations used to locate a target region positioned on a target that is to be imaged and within boundaries of a periphery of the housing. In some embodiments, the kit comprises a template configured to locate the target region based upon the location of the housing alignment indicators.

In one aspect, a method is provided. The method comprises, in some embodiments, positioning a device comprising a housing comprising an imaging unit and a working side such that the working side is adjacent target that is to be imaged; and activating a marking unit to produce a mark on the target to be imaged within the boundaries of a periphery of the housing.

In certain embodiments, the method comprises positioning a device comprising a housing comprising an imaging unit and a plurality of housing alignment indicators adjacent a target that is to be imaged; making marks at the plurality of alignment indicators; positioning a template based upon the location of the marks; and locating a target region based upon the position of the template.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
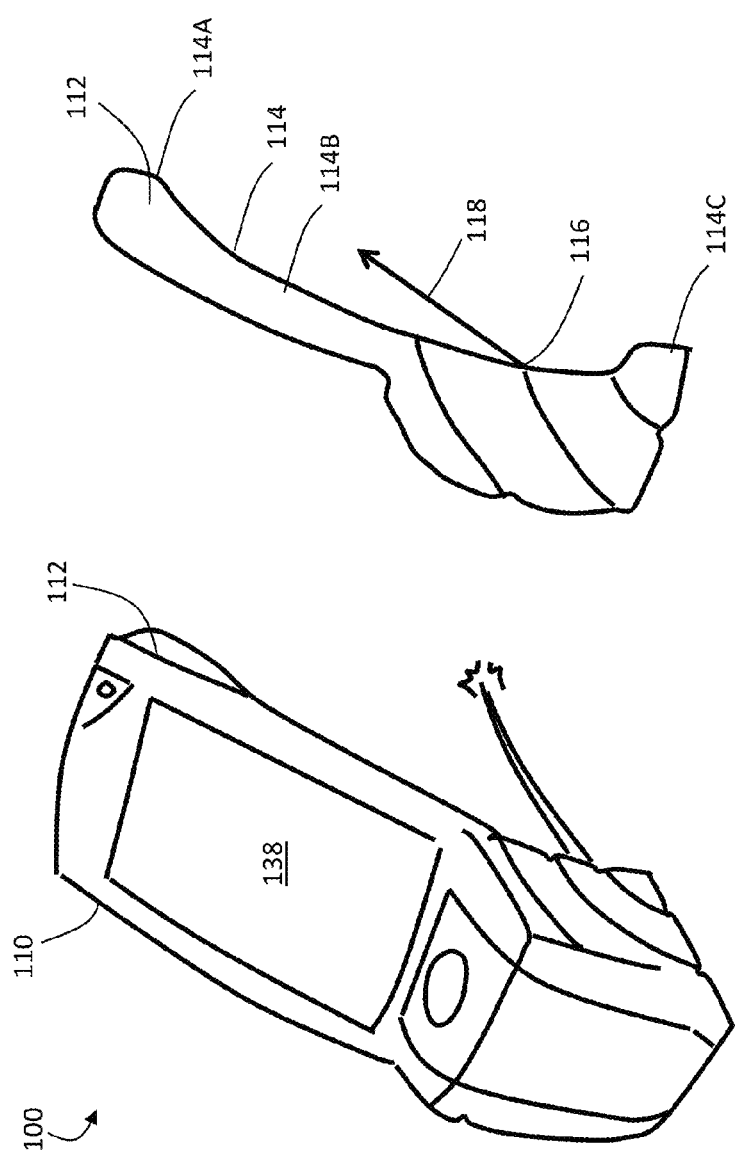
FIGS. 1-5C are schematic illustrations of imaging devices, according to certain embodiments.

Systems and methods related to the location of target regions in imaging applications are generally described. Certain embodiments relate to devices and methods for image-guided identification of suitable regions at which to insert needles, catheters, and the like. Such systems and methods can be used in association with a variety of imaging technologies, including ultrasound imaging. In certain embodiments, the systems and methods described herein can be used in association with hand-held ultrasound imaging devices.

It has been discovered, within the context of certain embodiments of the invention, that needle placement methods used with many current ultrasound devices are limited in effectiveness. For example, various types of needle guides have been designed. Typically these devices are co-operably detachable from the ultrasound imaging device. The needle guide can help to align the needle along the ultrasound scan plane at a fixed angle. However, such devices generally suffer from a number of limitations. First, alignment of needle insertion point with underlying anatomy is challenging with these devices because the transducer device is typically separate from the display screen. Second, the method does not facilitate the "marking approach" because it allows for a guide along only one side of the imaging device. If the procedure requires needle insertion in a location that the imaging device occupies when performing imaging, and thus while making the mark, then the mark made along the needle guide path will not correspond to the correct needle insertion location. Additionally, since there is only one guide, and thus one mark, the relative distance from the mark to the correct insertion point is challenging to localize. Lastly, the needle guides are restrictive as they encapsulate the needle and allow only a fixed angle during needle insertion. If the physician starts at one angle, and then wishes to change to a new angle, the presence of the needle guide around the needle prevents changing the angle.

Certain systems and methods described herein address one or more of the above limitations, and allow for more accurate and precise identification and marking of points of interest, such as insertion points for injection procedures and other medical procedures. In one set of embodiments, a marking unit associated with an imaging device is activated to produce a mark on the target that is to be imaged. The mark can be produced, for example, in a location adjacent the working side of the imaging device. Activating the marking unit can comprise, for example, pressing a button or releasing a trigger, which can cause a laser, a mechanical indentation unit, a lancing unit, a pen, an ink-based marker, or any other suitable marking device to produce a mark adjacent the working side. In another set of embodiments, an imaging device includes a plurality of alignment indicators configured to indicate reference locations and a template (either integrated with the imaging device or in a kit along with the imaging device) configured to locate a target region based upon the location of the housing alignment indicators. Such units can be used, for example, by aligning the imaging unit in a desired location, making a plurality of marks at the alignment indicators, positioning the template such that the alignment indicators are aligned with the template indicators, and marking the target location based upon the location of the template.

FIG. 1 includes schematic illustrations of an imaging device 100 that produces a mark using a marking unit, according to one set of embodiments. Device 100 comprises a housing 110. Housing 110 includes an imaging unit 112 and a working side 114. Imaging unit 112 can comprise, for example, at least one ultrasound transducer. The imaging unit can be configured to generate energy directed into the imaged target (e.g., the tissue of a subject) and/or configured to receive a portion of the energy reflected by a target located within the imaged target. For example, in cases in which an ultrasound transducer is employed, the transducer can be configured to generate ultrasonic energy, direct the ultrasonic energy into the imaged target, and/or receive a portion of the ultrasonic energy reflected by a target located within the imaged target. In certain embodiments, the imaging unit can comprise a plurality of ultrasound transducers arranged in an array.

Working side 114 can be configured to be placed adjacent a target that is to be imaged. For example, during use of the imaging device, the imaging device can be positioned such that the working side is adjacent to the target that is to be imaged. In one set of embodiments, when a portion of working side 114 is placed against the skin of a person, imaging unit 112 can be used to produce an image of the portion of the person underlying the skin with which the portion of the working side is in contact. The working side of an imaging device includes the surfaces of the imaging device that face the target that is to be imaged during operation of the imaging device. Thus, surfaces that are not in direct contact with the imaged target, but otherwise face the imaged target during operation, are considered to be part of the working side of the imaging device. For example, in FIG. 1, all of surface portions 114A, 114B, and 114C are part of working side 114, even though, in some embodiments, only surface portion 114A and 114C are in direct contact with the imaged target during operation of imaging device 100.

Device 100 can further comprise a marking unit configured to produce a mark on the target to be imaged. The mark can be produced, for example, upon activation of the marking unit. Activation of the marking unit can be configured, in some embodiments, to automatically produce a mark on the target to be imaged upon activation of an actuator, as described in more detail below.

A variety of types of marking units can be employed in the embodiments described herein. For example, in FIG. 1, marking unit 116 comprises a laser. The laser can be configured to emit electromagnetic radiation 118 that produces a discoloration on the target that is to be imaged. For example, in certain embodiments, upon activating the laser, electromagnetic radiation is emitted from the laser. The radiation can cause a discoloration (permanent or temporary) on the skin on which the laser is incident. Examples of lasers that are capable of making such discolorations include, but are not limited to $CO_2$ lasers or other lasers capable of creating a high-energy, focused excitation capable of discoloring skin, for example, due to heat.

In other embodiments, the laser is configured to produce a reflection of electromagnetic radiation, rather than a discoloration, on the target that is to be imaged. In some such embodiments, upon activating the laser, a laser spot is visible on the target that is to be imaged. Reflections of electromagnetic radiation can be produced by the laser by operating the laser at low power and within the visible spectrum of electromagnetic radiation. Focusing the laser can be used to generate a small visible reflection the laser energy along the skin surface. In certain embodiments, the user can use the visible reflection as an indication of the appropriate marking location. A mark can be created along the surface of the imaged target (e.g., along skin) using an ink-based marker, a pen, a lancing object, a mechanical indentation unit, or any other suitable device at the location of the focused laser light.

Figure 2:
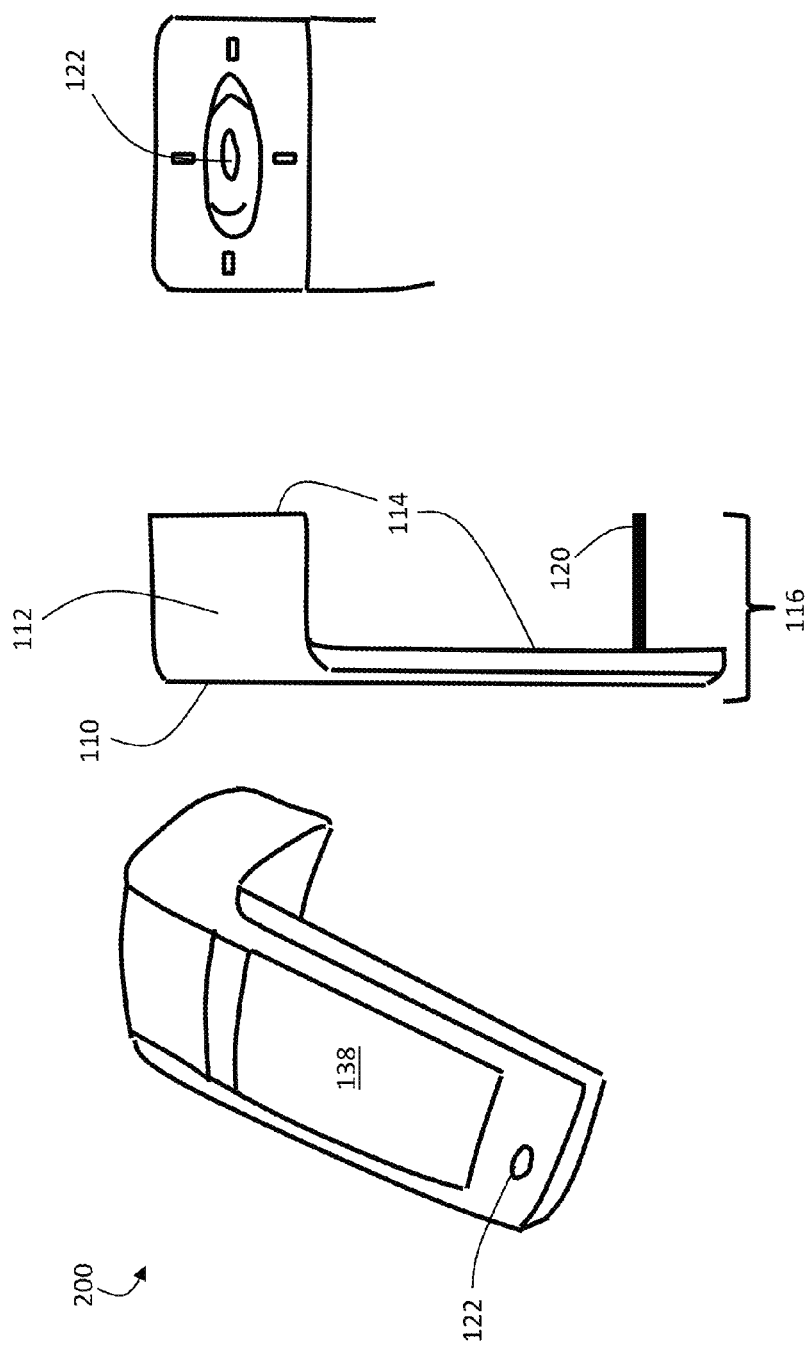

In some embodiments, the marking unit comprises a mechanical indentation unit. The mechanical indentation unit can be configured to produce an indentation on a surface of the target that is to be imaged. For example, in FIG. 2, imaging device 200 includes a marking unit 116 comprising mechanical indentation unit 120. When indentation unit 120 is activated (e.g., by depressing button 122), mechanical indentation unit 120 can be extended from housing 110 such that it produces an indentation on the imaged surface (e.g., skin). The mark produced by the mechanical indentation can correspond to a discoloration produced due to the application of mechanical pressure.

Figure 3:
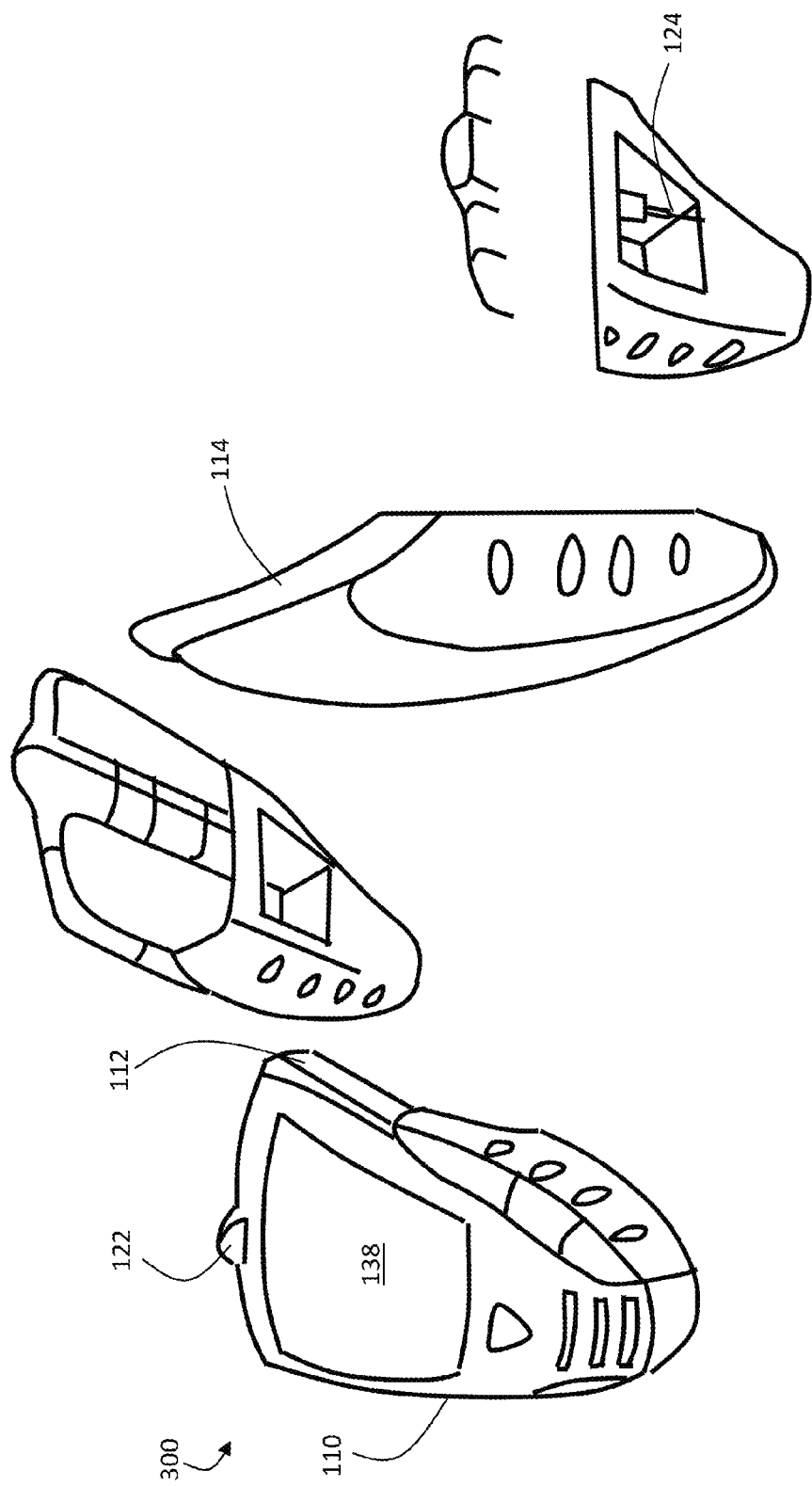

The marking unit comprises, in certain embodiments, a lancing unit. The lancing unit can be configured to penetrate a surface of the target that is to be imaged. For example, in FIG. 3, imaging device 300 includes a marking unit 116 comprising lancing unit 124. When lancing unit 124 is activated (e.g., by depressing button 122), lancing unit 124 can be extended from housing 110 such that it penetrates the imaged surface (e.g., skin).

Figure 4:
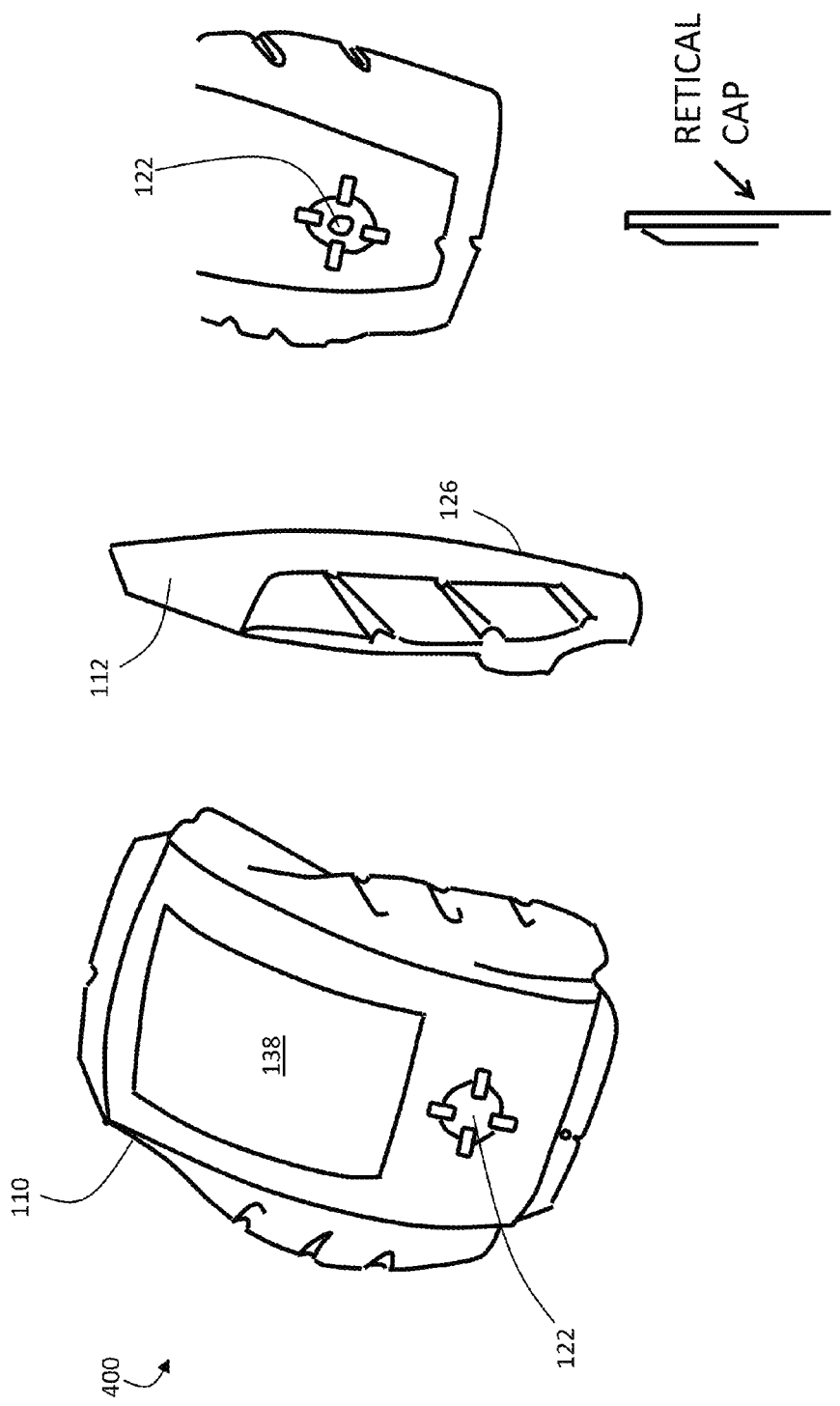

In still other embodiments, the marking unit can be configured to deposit a material on the target that is to be imaged. As one particular example, the marking unit can be configured to deposit ink on the imaged target. For example, in FIG. 4, imaging device 400 includes a marking unit 116 comprising a material-deposition member 126, such as a pen. When marking unit 116 is activated (e.g., by depressing button 122), member 126 can be extended from housing 110 such that it deposits a material such as ink onto the imaged surface (e.g., skin).

While embodiments have been illustrated in which the marking unit and the housing are monolithically integrated (i.e., such that one cannot be separated from the other without substantially damaging one or both the of the housing and the marking unit), it should be understood that the present disclosure is not so limited. In certain embodiments, the marking unit is detachably coupled to the housing, such that one can be removed from the other without causing substantial damage to either.

In certain embodiments, the imaging device comprises an actuator configured to activate the marking unit when the actuator is activated. In certain embodiments, once the actuator has been activated, the mark is automatically made on the underlying surface of the target that is to be imaged, without further action needed from the user. For example, in the embodiments illustrated in FIGS. 1-4, the imaging devices include button 122, which activates the marking unit when depressed. In other embodiments, a trigger or other type of actuator can be used to activate the marking unit.

Figure 5B:
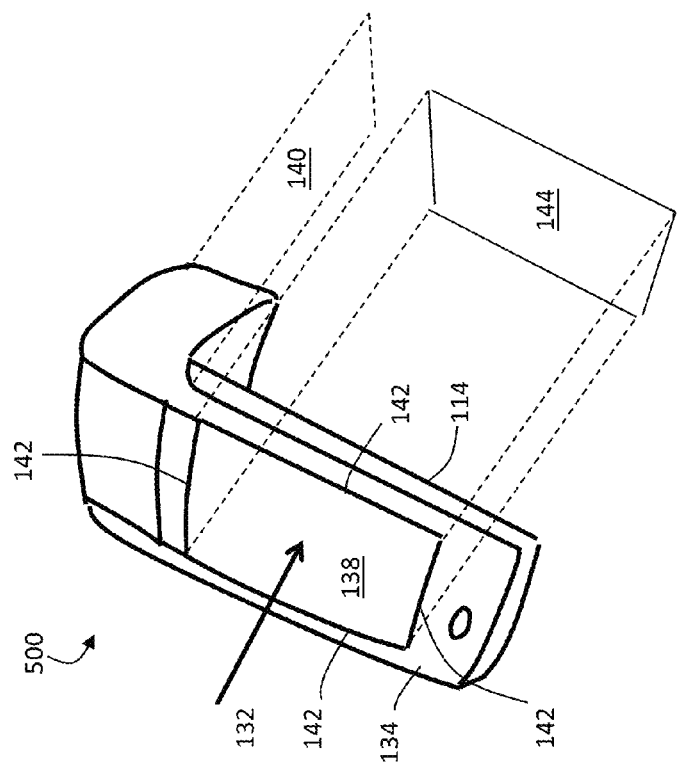
Figure 5A:
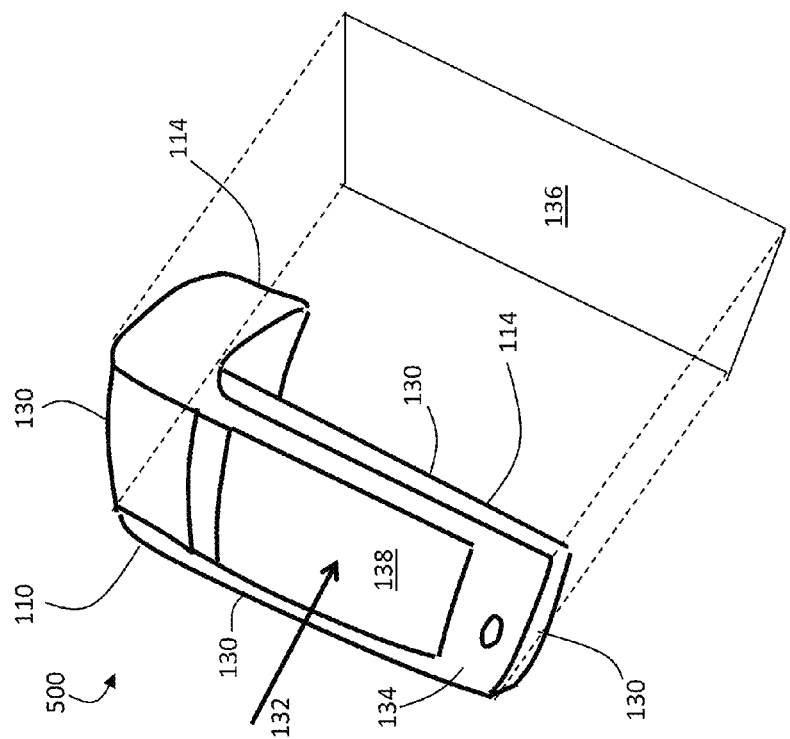

In some embodiments, the marking unit is configured to produce a mark on the target to be imaged (e.g., on the skin) and within the boundaries of the periphery of the housing. The boundaries of the periphery of the housing are generally defined by the edges of the housing when viewed from the side of the housing that is opposite the working side. Accordingly, when a mark is made within the boundaries of the periphery of the housing, the mark is made at a location on the target that is covered by the housing during operation. FIG. 5A illustrates this principle. In FIG. 5A, imaging device 500 includes housing 110, which includes boundaries 130 that define the periphery of housing 110. When viewed in the direction of arrow 132 (i.e., when viewing device 500 from side 134, which is opposite working side 114), area 136 is covered by device 500. Accordingly, in FIG. 5A, all points within area 136 are within the boundaries of the periphery of the housing.

In certain embodiments, the marking unit can be configured to produce a mark on the target to be imaged (e.g., on the skin) and within the imaging plane of the imaging device. Generally, the imaging plane of the imaging device refers to the plane along which the imaging unit collects data to produce the image. For example, in the case of an ultrasound imaging unit, the imaging plane refers to the plane along which the ultrasound transducer emits ultrasonic radiation and receives feedback from the ultrasonic radiation to produce a 2-dimensional image (e.g., when an ultrasound imaging device is operated in "B-mode," as described below). In many embodiments, including many ultrasound imaging embodiments, the imaging plane is perpendicular to the external surface of the imaged target. In the set of embodiments illustrated in FIG. 5B, the imaging plane is illustrated as plane 140.

In certain embodiments, the imaging device comprises an output display covering at least a portion of a surface of the housing opposite the working side. For example, in FIGS. 1-5B, the imaging devices include output displays 138, which cover a portion of surface 134 (which is opposite working side 114). The display can be configured to present information indicative of a position of the target to be imaged. For example, when used to image a subject, the display can be configured to present information indicative of a position of a bone within the imaged subject. Any suitable type of display can be used as output display 138. Exemplary types of output displays that can be used include, but are not limited to, color super twisted nematic (CSTN) displays, thin film transistor (TFT) displays, thin film diode (TFD) displays, organic light-emitting diode (OLED) displays, active-matrix organic light-emitting diode (AMOLED) displays, and the like.

In some embodiments, the marking unit can be configured to produce a mark on the target to be imaged (e.g., on the skin) and within the boundaries of the periphery of the output display. The boundaries of the periphery of the output display are generally defined by the edges of the output display when viewed from the side of the housing that is opposite the working side. Accordingly, when a mark is made within the boundaries of the periphery of the output display, the mark is made at a location on the target that is covered by the output display during operation. FIG. 5B illustrates this principle. In FIG. 5B, device 500 includes output display 138, which includes boundaries 142 that define the periphery of the output display. When viewed in the direction of arrow 132 (i.e., when viewing device 500 from side 134, which is opposite working side 114), area 144 is covered by output display 138. Accordingly, in FIG. 5B, all points within area 144 are within the boundaries of the periphery of the output display.

As noted above, output display 138 can be used to display images of the imaged target. For example, in some embodiments, the imaging device can be configured to produce a 2-dimensional cross-sectional image of the underlying target that is to be imaged on the output display, as might be produced, for example, by a 2-dimensional ultrasound device. Generally, in such embodiments, the cross-sectional image that is produced is perpendicular to the exterior surface of the imaged target (i.e., the surface of the imaged target against which the unit is placed to produce the image).

The imaging device can be configured, in some embodiments, to produce a 3-dimensional reading of the underlying target that is to be imaged. In some such embodiments, output display 138 can be configured to display an image corresponding to a cross-section of the imaged target along any surface portion that has been imaged by the imaging unit. One of ordinary skill in the art is familiar with such units. Briefly, such imaging units can be used to make a plurality of 2-dimensional images corresponding to cross-sections that are perpendicular to the surface of the target against which the imaging unit is placed during operation. Once the 2-dimensional images have been produced, the 2-dimensional images can be assembled (e.g., using a computer processor) to produce a 3-dimensional array of data. Using the 3-dimensional array of data, cross-sectional images along any plane within the 3-dimensional space (including cross-sections parallel to the surface of the target against which the imaging unit is placed during operation, such as when an ultrasound imaging device is operated in "C-mode," as described below) can be produced. For example, cross-sectional images of the underlying tissue can be produced using such devices such that the images are parallel to the skin of the subject being imaged.

Figure 5C:
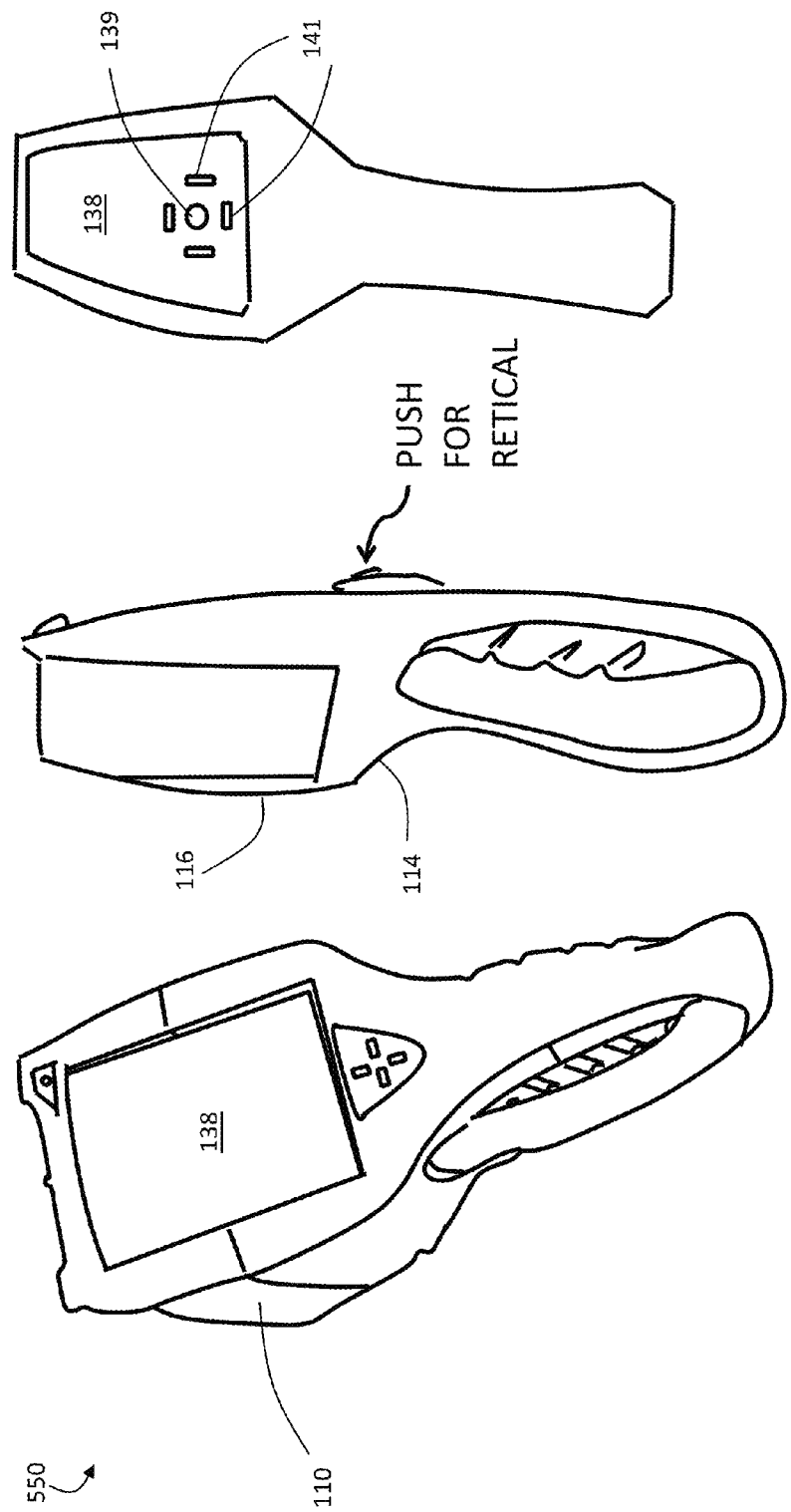

FIG. 5C is a schematic illustration of an imaging device 550 comprising a marking unit configured to produce a mark within the boundaries of the periphery of output display 138. In FIG. 5C, marking unit 116 is positioned on working side 114 of device 550 such that it lies underneath output display 138 when device 550 is in use. Accordingly, when marking unit 116 is activated, it produces a mark corresponding to region 139 on output display 138. The ability to place a mark within the boundaries of the output display can allow for relatively easy placement of the mark next to a desired target location. For example, in certain embodiments, output display 138 can include reference markers 141, which can indicate the location where the mark will be placed by marking unit 116. In embodiments in which output display 138 is configured to display a map of the underlying imaged target (e.g., when device 550 is a 3-dimensional imaging unit, and the image on output display 138 corresponds to a surface parallel to the exterior surface of the imaged target), reference markers 141 can be aligned with the desired target location shown on the output display. After alignment of reference markers 141, activation of marking unit 116 can produce a mark on the underlying imaged target at the desired location.

Marking unit 116 can be configured to produce a mark within the boundaries of the periphery of the housing, within the boundaries of the output display, or within the imaging plane of the imaging unit using a variety of methods. For example, the marking unit can be configured to produce a mark in a desired location by positioning the marking unit on working side 114 in the desired location and configuring the marking unit to produce the mark directly underneath the imaging device. For example, the marking unit can be configured to produce a mark within the boundaries of the periphery of the output display by positioning the marking unit within the boundaries of the output display, as illustrated in FIG. 5C. In other embodiments, the marking unit can be configured to produce a mark in a desired location by positioning the marking unit outside the desired location and orienting the marking unit at an angle such that the mark is placed at a location that is not directly underneath the marking unit. For example, the marking unit can be configured to produce a mark within the boundaries of the periphery of the output display by positioning the marking unit outside the boundaries of the output display but angling the marking unit such that the mark is made within the boundaries of the output display, as illustrated in FIG. 1.

As noted above, in one set of embodiments, the imaging device can include a plurality of alignment indicators configured to indicate reference locations on a target to be imaged. In certain embodiments, the imaging device can also comprise a template configured to locate a target region based upon the location of the housing alignment indicators. In other embodiments, a kit containing the imaging device can also contain a separate template configured to locate a target region based upon the location of the housing alignment indicators.

Figure 6A:
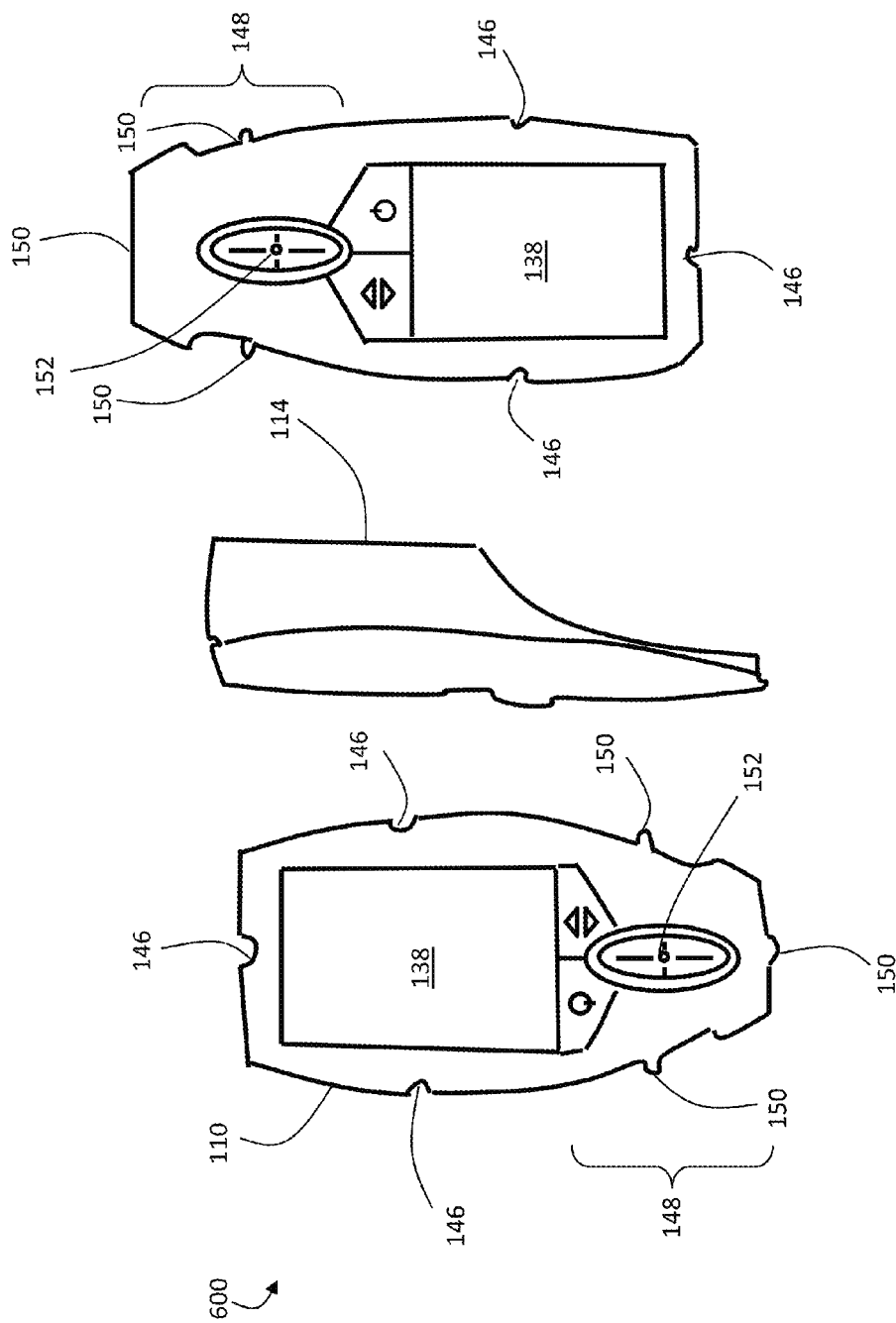
FIGS. 6A-7C are, according to some embodiments, schematic illustrations of imaging device including target region location templates.

FIG. 6A is an exemplary schematic illustration of an imaging device 600 including housing alignment indicators 146. Housing alignment indicators 146 can be configured to indicate reference locations used to locate a target region that is positioned on the target to be imaged and within boundaries of a periphery of the housing. For example, in FIG. 6, housing alignment indicators 146 can be used to triangulate a target position at a location underneath the center of output display 138 (which is within the boundaries of the periphery of the housing and within the boundaries of the periphery of the output display).

Device 600 also includes a template 148 configured to locate the target region based upon the location of the housing alignment indicators. Template 148 can comprise a plurality of template alignment indicators 150. The positions of template alignment indicators 150 can correspond to the positions of housing alignment indicators 146. For example, in FIG. 6A, template alignment indicators are positioned such that they are spaced in a substantially similar fashion as housing alignment indicators 146. In FIG. 6A, the three housing alignment indicators are positioned to form a triangle, and the three template alignment indicators are positioned to form substantially the same triangle.

Template 148 can also comprise a target region indicator 152. The target region indicator can take a variety of forms. For example, in FIG. 6A, target region indicator 152 comprises a hole formed through the template. In other embodiments, the target region indicator comprises a marking unit that is integrated with the template. In some such embodiments, a marking unit (e.g., a laser, an ink-based marker, a pen, a lancing object, or a mechanical indentation unit, which can be similar to those integrated with the housing, as described above in relation to FIGS. 1-4) can be integrated into the template. The marking unit integrated with the template can be activated, for example, by depressing a button on the template, activating a trigger on the template, or via any other suitable method.

Figure 6C:
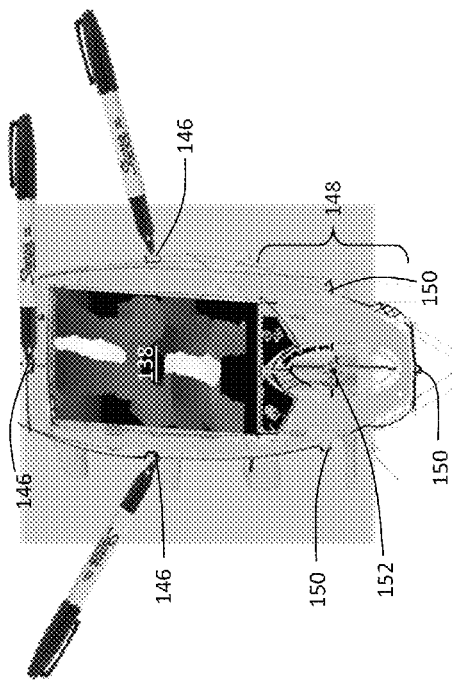
Figure 6E:
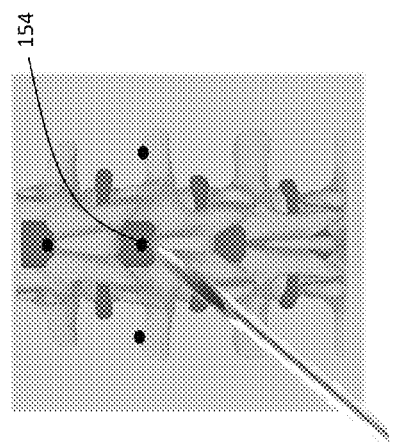
Figure 6B:
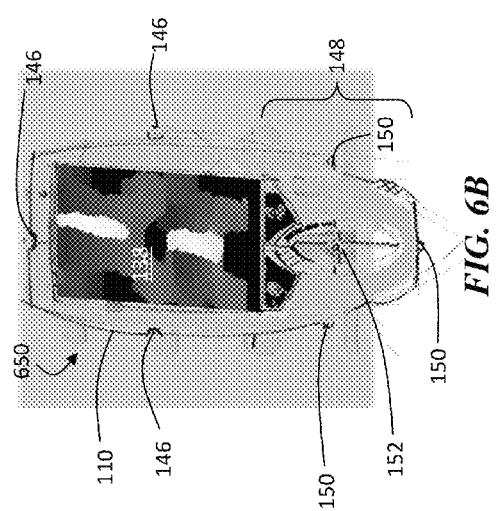
Figure 6D:
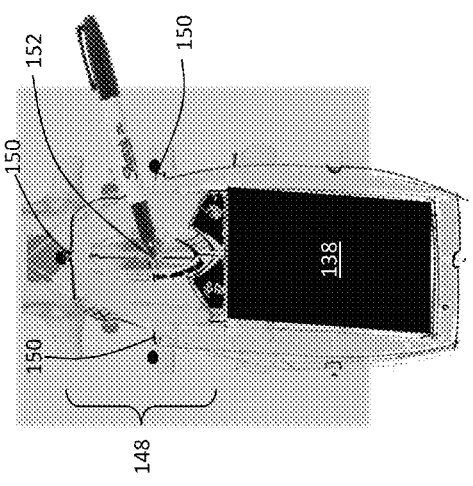

FIGS. 6B-6E are schematic illustrations outlining the operation of an exemplary imaging device 650. In FIG. 6B, device 650 includes three housing alignment indicators 146 configured to indicate reference locations that can be used to locate a target region. In the case of FIG. 6B, the target location is near the center of output display 138. Once device 650 has been properly positioned, marks can be made at the plurality of housing alignment indicators, as illustrated in FIG. 6C. While the use of ink-based markers is illustrated in FIG. 6C, it should be understood that marks can be made via any suitable method including, but not limited to, making discolorations (e.g., using a laser), making indentations, and/or depositing a material (including non-ink materials). Once the marks have been made at the housing alignment indicators, the template can be positioned based upon the location of the marks. Positioning the template can comprise aligning the marks with template alignment indicators, as illustrated in FIG. 6D.

Once the template has been positioned, the target region can be located based upon the position of the template. Locating the target region can comprise locating a target region location feature of the template, such as hole 152 in FIG. 6D. In certain embodiments, locating the target region comprises making a mark at the target region location feature of the template. For example, in FIG. 6D, once template 148 has been positioned, a material (e.g., ink) can be deposited (e.g., using a pen) to mark the target location on the target being imaged. In other embodiments, a laser, a mechanical indentation unit, a lancing unit, a needle, a pen, or any other suitable marking unit can be used to produce a mark at the target region.

In some embodiments, locating the target region comprises inserting an elongated object, such as a needle, through the target region location feature of the template. In certain embodiments, a needle guide can be built in to a template or can be attachable to a template. Optionally, the template can be integrated with the housing, as illustrated in FIGS. 6A-7C. For example, in FIG. 6D, a needle can be threaded through hole 152 in template 148, such that hole 152 is used as a needle guide. The needle can then be used to inject and/or withdraw fluid while template 148 remains in place.

In other embodiments, locating the target region can comprise activating a marking unit on the template. For example, in one set of embodiments, once the template has been aligned with the marks corresponding to the positions of the housing alignment indicators, a marking unit integrated with the template can be activated (e.g., by depressing a button on the template, activating a trigger on the template, or via any other suitable mechanism). Once activated, the marking device on the template can produce a mark at the target location (e.g., using a laser, an ink-based marker, a pen, a mechanical indentation unit, a lancing unit, or any other suitable mechanism).

In some embodiments, once a mark has been made at the target region, the mark at the target region can be used to guide the insertion of a needle or other elongated object. For example, in FIG. 6E, a needle is inserted through the skin proximate mark 154, which is positioned over the target region.

As noted elsewhere, the plurality of housing alignment indicators can be configured to locate a target region that is positioned on the target to be imaged and within boundaries of a periphery of the housing. For example, in FIGS. 6B-6E, housing alignment indicators 146 are positioned along the periphery of housing 110 and can be used to triangulate a position that lies within the boundaries of the periphery of the housing. In certain embodiments, including the embodiment illustrated in FIGS. 6B-6E, the plurality of housing alignment indicators are configured to locate a target region that is positioned on the target to be imaged and within the boundaries of the periphery of the output display, for example, by positioning the housing alignment indicators at positions along the periphery of the output display. In other embodiments, the plurality of housing alignment indicators are configured to locate a target region that is positioned on the target to be imaged and within an imaging plane of the imaging unit. This can be achieved, for example, by positioning the housing alignment indicators along the periphery of the imaging unit (e.g., along the periphery of an ultrasonic transducer).

The template and the housing can be attached to each other, in certain embodiments. In some such embodiments, the template and the housing can be fixedly attached to each other, such that neither the template or the housing can be removed from the other without damaging the template and/or the housing. In other such embodiments, the template and the housing are detachably coupled such that they can be removed from each other without damaging either.

Figure 6F:
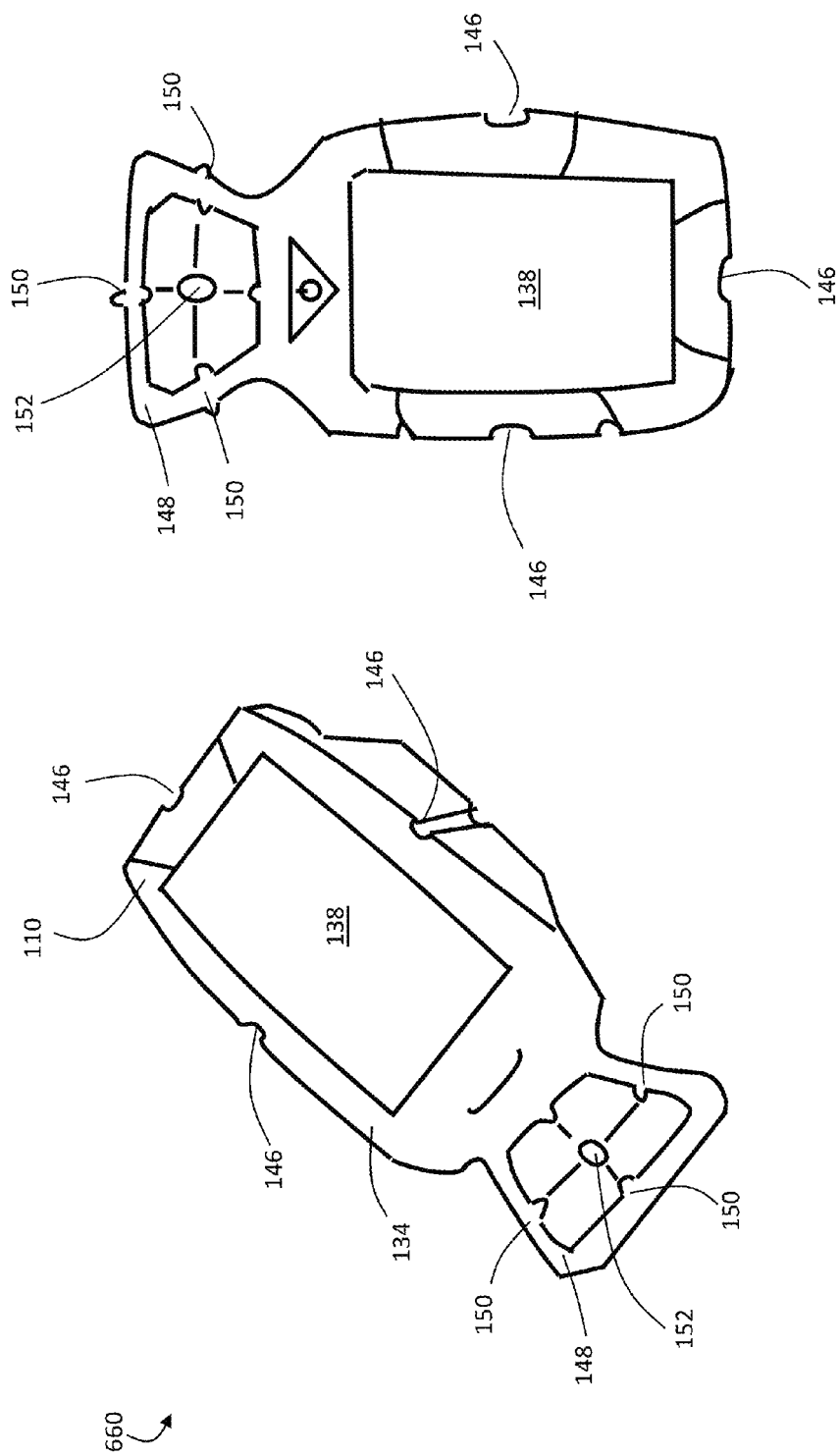
Figure 6G:
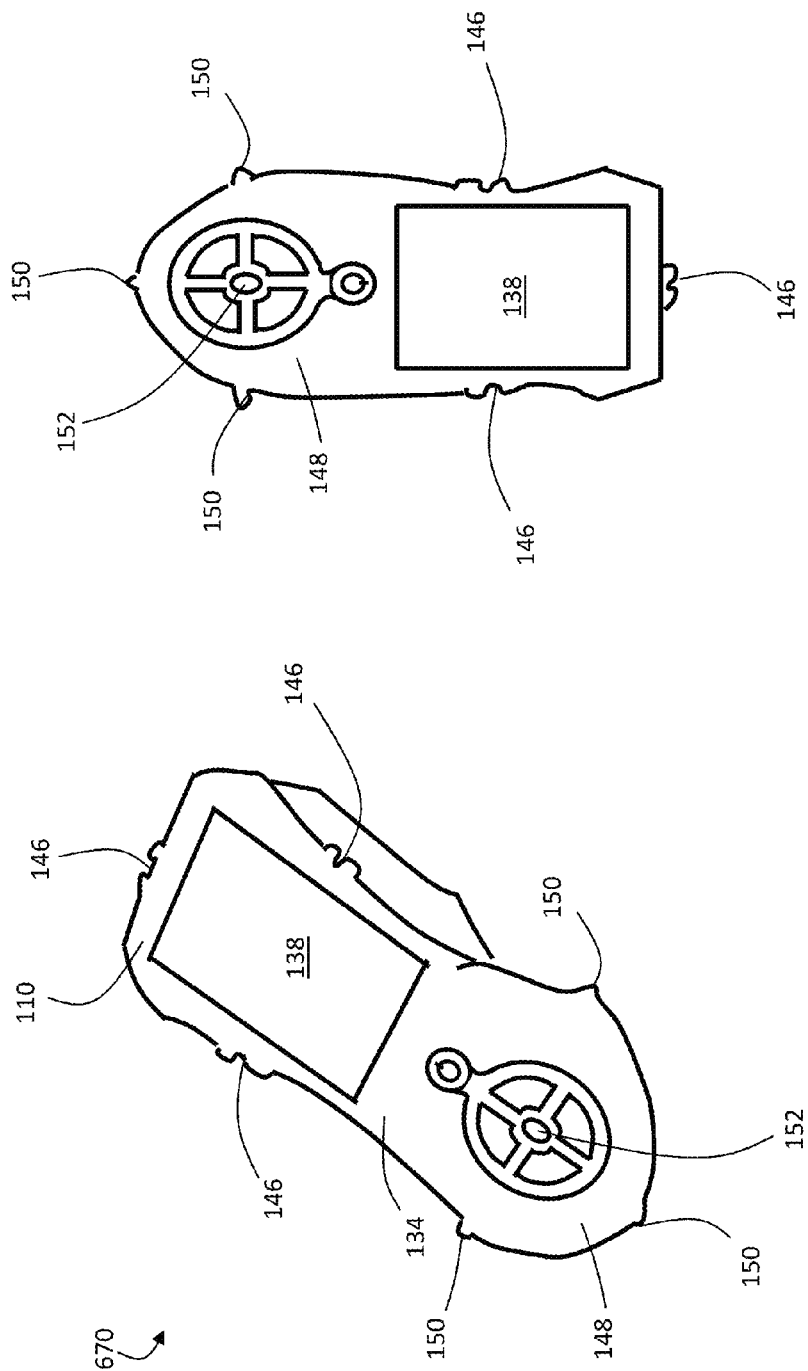
Figure 7A:
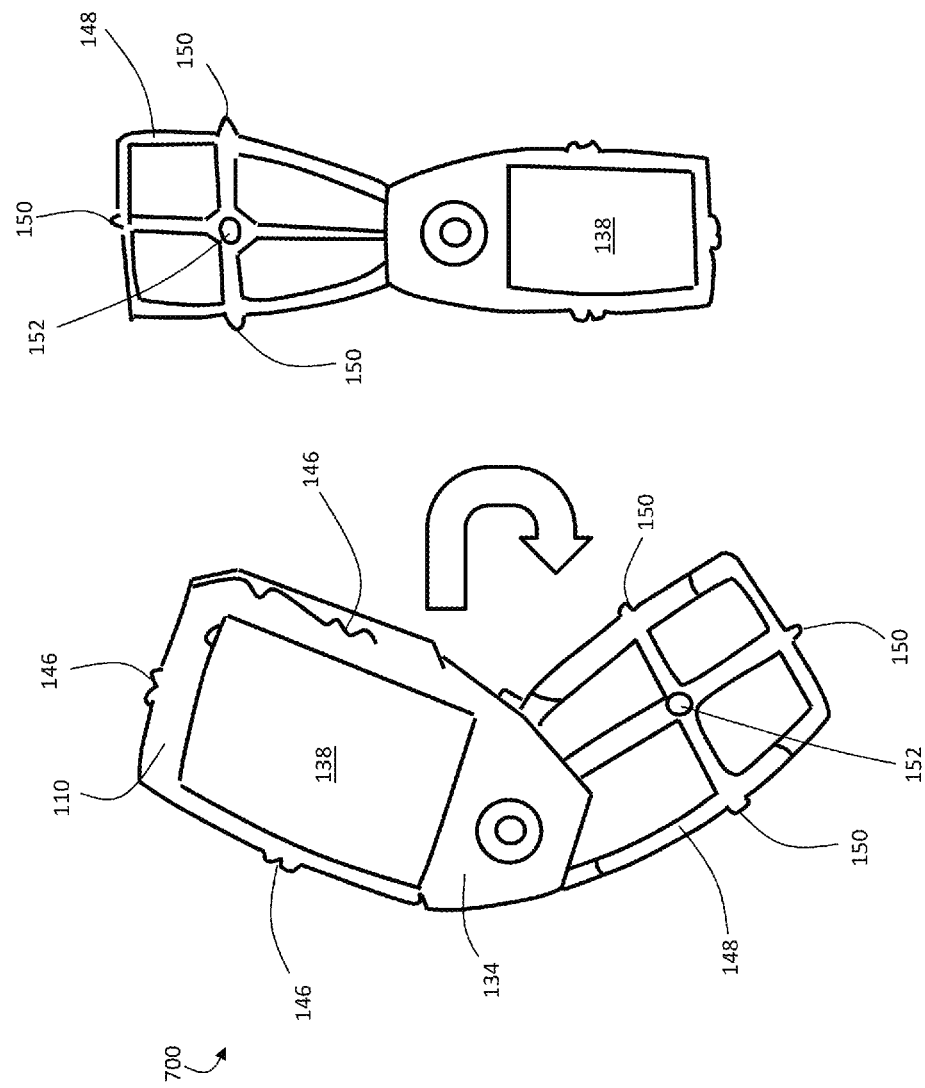
Figure 7B:
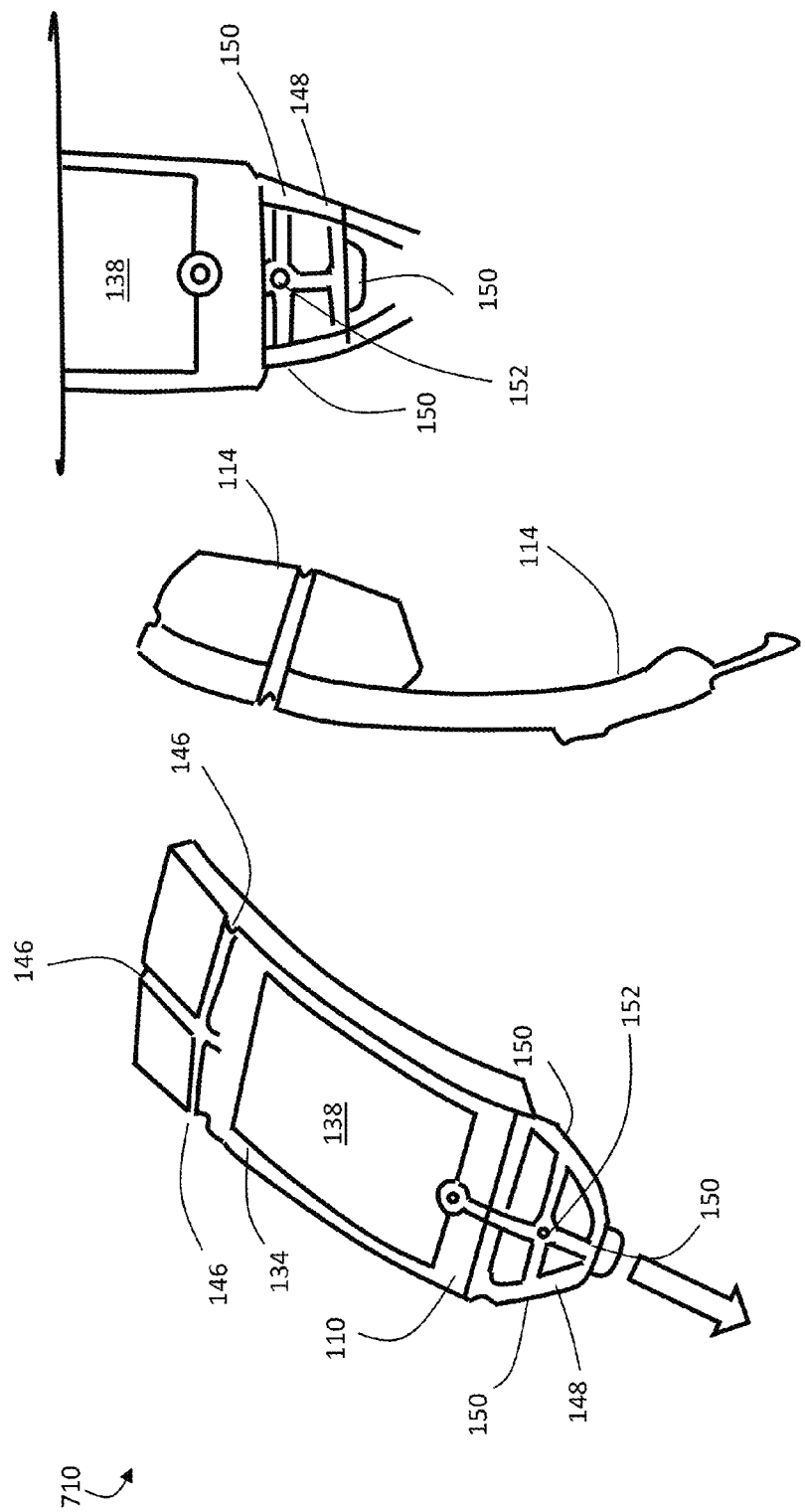
Figure 7C:
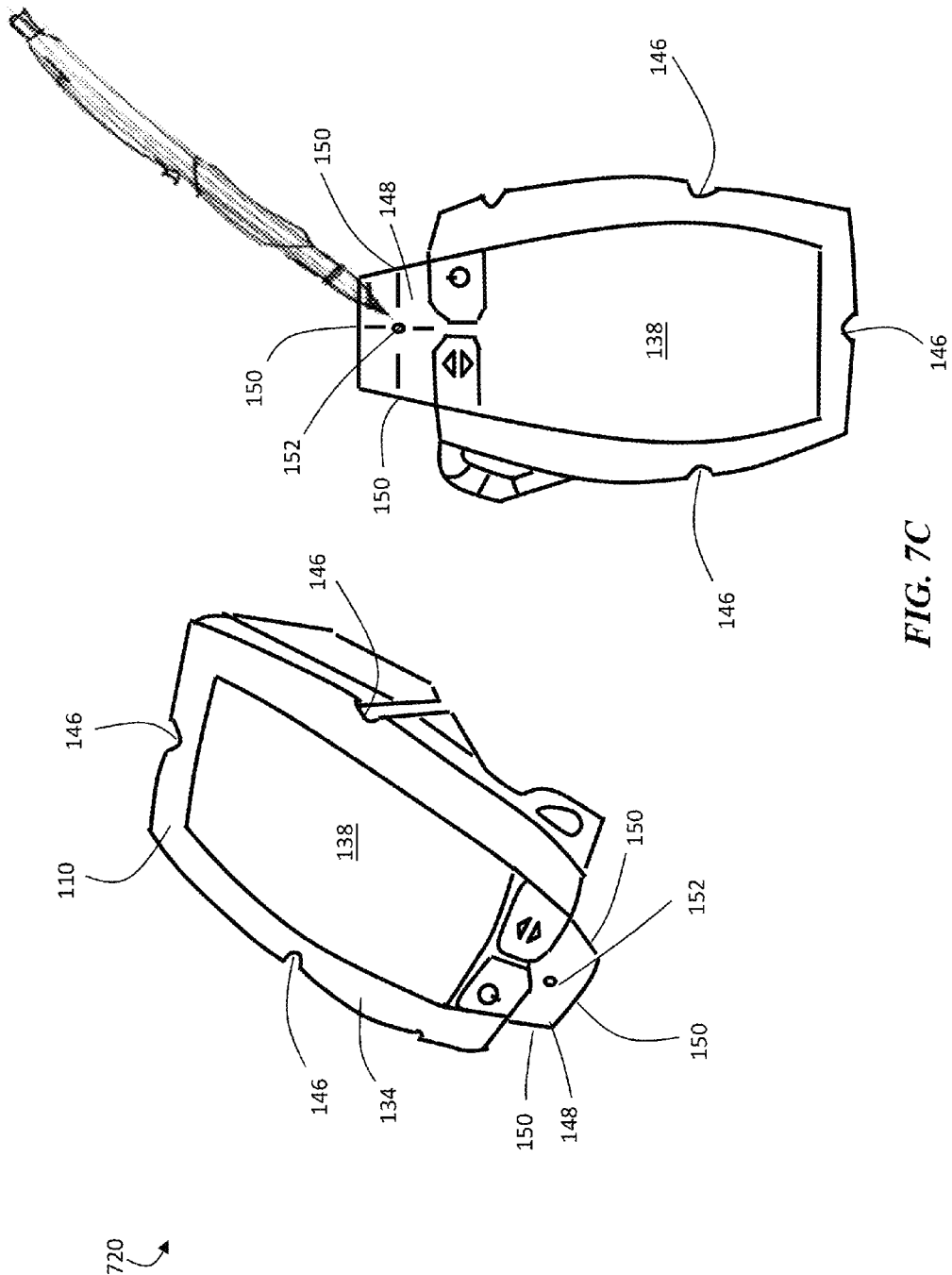

FIG. 6A includes a schematic illustration of an imaging device 600 in which the template 148 is fixedly attached to the housing. Specifically, in FIG. 6A, template 148 is integrated within the handle of the device. FIGS. 6F-6G are schematic illustrations of other device 660 and 670, respectively, in which the template is integrated within the handle of the device.

In other embodiments, the template can be configured to be retracted from a first position relative to the housing to a second position relative to the housing. In some such embodiments, the template can be configured to be rotatably retracted from a first position relative to the housing to a second position relative to the housing. For example, in imaging device 700 of FIG. 7A, template 148 is configured such that it can be rotatably retracted from a first position in which the template is not positioned underneath the output display (as shown on the right-hand side of FIG. 7A) to a second position in which the template is positioned underneath the output display.

In other embodiments, the template can be configured to be retracted from a first position relative to the housing to a second position relative to the housing by sliding the template linearly with respect to the housing. For example, in imaging device 710 of FIG. 7B, template 148 is configured such that it can be retracted from a first position in which the template is not positioned underneath the output display (as shown in each of the illustrations in FIG. 7B) to a second position in which the template is positioned underneath at least a portion of the output display by linearly sliding the template into the housing.

In still other embodiments, the template can be configured to be retracted from a first position relative to the housing to a second position relative to the housing by flipping the template around an axis into the housing. For example, in imaging device 720 of FIG. 7C, template 148 is configured such that it can be retracted from a first position in which the template is not positioned underneath the output display (as shown in each of the illustrations in FIG. 7C) to a second position in which the template is positioned underneath at least a portion of the output display by flipping the template such that the template rotates around a shaft threaded through the base of the template.

Figure 8:
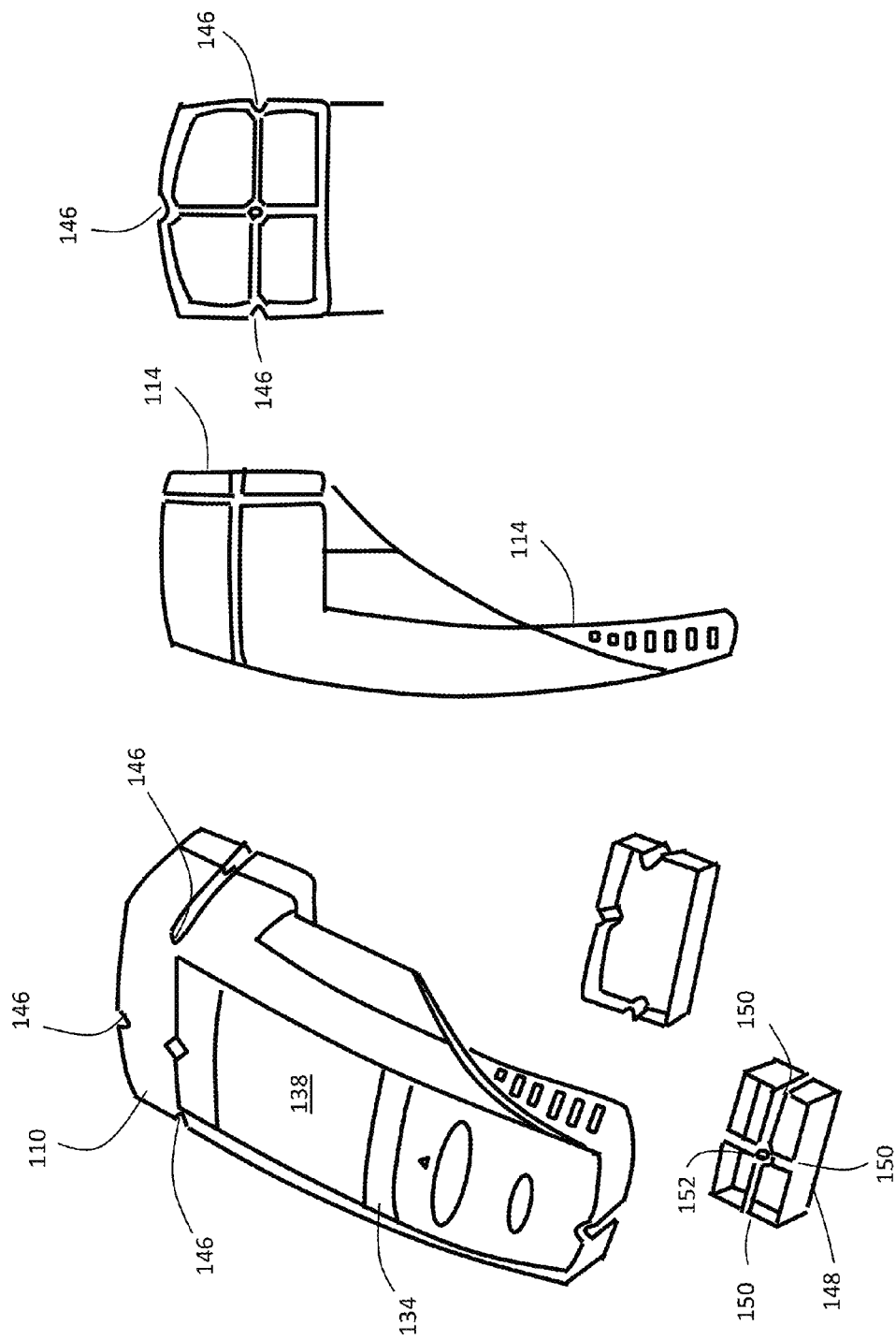
FIG. 8 is a schematic illustration of an imaging device and a separate target region location template, according to one set of embodiments.

In other embodiments, the template and the housing can be separate, distinct units. For example, in FIG. 8, housing 110 and template 148 are separate units. Housing 110 and template 148 can be included, for example, in a kit. In certain embodiments, template 148 can be a disposable device that is attachable/detachable from the main housing. Template 148 could also be a disposable device that is completely separate from the main housing. In certain embodiments, the disposable template can include a marking unit (which can be automatic), including any of the marking units described above (e.g., an ink-based marker, a pen, a lancing object, a mechanical indentation unit, or a laser). Optionally, the marking unit can be activated by depressing a button, releasing a trigger, or by any other suitable mechanism. When the disposable template has been properly located (e.g., using the marks corresponding to the locations of the housing alignment indicators), the marking unit on the template can be activated to discolor or otherwise mark the underlying skin.

Housing alignment indicators 146 can be of any suitable form. For example, in FIG. 6A, housing alignment indicators 146 comprise indentations into the housing unit. It should be understood, however, that the embodiments described herein are not so limited. For example, the housing alignment indicators can comprise protrusions from the housing unit. In some such embodiments, one can make reference marks next to the protrusions. In certain embodiments, the housing alignment indicators can comprise holes within the housing unit. In some such embodiments, one can make reference marks by inserting a pen or other mark-making device through the holes. In some embodiments, the housing alignment indicators comprise visible markings on the housing unit. In some such embodiments, reference marks can be made adjacent the visible markings. In some embodiments, the housing alignment indicators can comprise a combination of the options outlined above.

In certain embodiments, the positions of the housing alignment indicators, relative to the housing, can be fixed. In other embodiments, the housing alignment indicators are moveable relative to the housing.

As illustrated in FIGS. 6A-8, the housing alignment indicators are positioned along the periphery of the housing. However, the invention is not so limited, and in other embodiments, the housing alignment indicators can be positioned at other locations within the housing.

Template alignment indicators 150 can also be of any suitable form. For example, in FIG. 6A, template alignment indicators 150 comprise protrusions from the housing unit. In certain embodiments, the template alignment indicators can comprise indentations into the template, holes within the template, or visible markings on the template. In some embodiments, the template alignment indicators can comprise a combination of the options outlined above.

In certain embodiments, the positions of the template alignment indicators, relative to the housing, can be fixed. In other embodiments, the template alignment indicators are moveable relative to the housing and/or the template.

As illustrated in FIGS. 6A-8, the template alignment indicators are positioned along the periphery of the template. However, the invention is not so limited, and in other embodiments, the template alignment indicators can be positioned at other locations within the template.

The embodiments described herein can be used in association with a variety of types of imaging devices. For example, in certain embodiments, the imaging device comprises an ultrasound imaging device. The embodiments described herein can also be used with other types of imaging systems including, but not limited to, x-ray based imaging systems, magnetic-based imaging systems, and the like. One of ordinary skill in the art would recognize that, in addition to the housing, imaging unit, output display, and other components of the imaging device described herein, a typical imaging device might also include a computer processing unit, an imaging processing circuit (e.g., an ultrasound processing circuit), a battery, a motion tracking circuit, and/or other components.

In certain embodiments, the imaging device can comprise a handheld ultrasound imaging device. One example of such a device is described in International Patent Application Publication No. WO2011/094585 by Mauldin et al., filed Jan. 28, 2011, published Aug. 4, 2011, and entitled "Ultrasound for Locating Anatomy or Probe Guidance," which is incorporated herein by reference in its entirety for all purposes. Such device can include, for example, at least one ultrasound transducer. The device might also include a motion tracking circuit. One or more of the ultrasound transducers can generate ultrasonic energy, which can be directed into the imaged target (a subject such as a human person). Some of the ultrasonic energy can be reflected by the target and returned to the ultrasonic transducer that originally produced the energy, or to another ultrasonic transducer in the array. The ultrasonic transducer(s) can be coupled to an ultrasonic signal conditioning circuit (such as a processor circuit or a memory circuit) via a bus. The ultrasonic signal conditioning circuit can include beamforming circuitry or other processing circuitry, which are known to those of ordinary skill in the art. In certain embodiments, the ultrasonic signal condition circuit can be configured to amplify, phase-shift, time-gate, filter, or otherwise condition received ultrasonic information (e.g., echo information). The receive path from each element in a transducer array can include one or more of a low noise amplifier, a main-stage amplifier, a band-pass or a low-pass filter, or an analog-to-digital converter. In certain embodiments, one or more signal conditioning steps can be performed digitally, such as using the processor circuit. Such processor circuitry can include one or more of a field-programmable gate array (FPGA) or other programmable logic devices (PLDs), a microprocessor, a system-on-chip including one or more execution cores or other circuitry, a microcontroller, or one or more or other circuits.

The ultrasonic imaging device can be configured to obtain imaging information from loci corresponding to portions on or nearby an anatomical target of interest, such as a bone (e.g., a portion of the spinous process). In some embodiments, the imaging device can be configured to obtain ultrasonic echo information corresponding to one or more planes perpendicular to the surface of an array of ultrasound transducers (e.g., to provide "B-mode" imaging information). In certain embodiments, the imaging device can be configured to obtain information corresponding to one or more planes parallel to the surface of the array of ultrasound transducers (e.g., to provide a "C-mode" ultrasound image of loci in a plane parallel to the surface of the transducer array at a specified depth within the tissue of the subject). In certain embodiments, the processor circuit can be coupled to one or more processor readable media, such as a memory circuit, a disk, or one or more other memory technology or storage devices.

U.S. Provisional Patent Application Ser. No. 61/662,481, filed Jun. 21, 2012 and entitled "Target Region Identification for Imaging Applications" is incorporated herein by reference in its entirety for all purposes.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/ or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "having," "containing," "involving," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device, comprising:
    a housing comprising:
        an imaging unit; and
        a working side including a first portion configured to be placed on a surface adjacent a target that is to be imaged and a recessed portion configured to form a gap between the recessed portion and the surface of the target when the first portion is disposed on the surface of the target;
    an output display covering at least a portion of a surface of the housing opposite the working side;
    an actuator on the surface of the housing opposite the recessed portion; and
    a marking unit disposed on the recessed portion of the housing and configured to produce a mark on the surface of the target to be imaged within boundaries of a periphery of the output display only when the actuator is activated while the first portion is disposed on the surface of the target.

2. The device of claim 1, wherein the actuator comprises a button.

3. The device of claim 1, wherein the imaging unit comprises an ultrasound transducer.

4. The device of claim 1, wherein the marking unit comprises a laser.

5. The device of claim 4, wherein the laser is configured to produce a discoloration on the target that is to be imaged.

6. The device of claim 4, wherein the laser is configured to produce a reflection of electromagnetic radiation on the target that is to be imaged.

7. The device of claim 1, wherein the marking unit comprises a mechanical indentation unit.

8. The device of claim 1, wherein the marking unit comprises a lancing unit.

9. The device of claim 8, wherein the lancing unit is configured to penetrate a surface of the target that is to be imaged.

10. The device of claim 1, wherein the marking unit is detachably coupled to the housing.

11. The device of claim 1, wherein the marking unit is configured to produce the mark within an imaging plane of the imaging unit.

12. The device of claim 1, wherein the display includes physical reference markers that indicate a location on the target to be marked by the marking unit.

13. The device of claim 7, wherein the mechanical indentation unit includes a shaft extending from the recessed portion, the shaft having a length less than or equal to a length of the gap.

14. The device of claim 7, wherein the output display displays a map of the target.

\* \* \* \* \*